US00PP32620P2

(12) United States Plant Patent
Suiker

(10) Patent No.: US PP32,620 P2
(45) Date of Patent: Dec. 15, 2020

(54) ***FRAGARIA* PLANT NAMED 'FALCO'**

(50) Latin Name: ***Fragaria* x *ananassa***
Varietal Denomination: Falco

(71) Applicant: Flevo Berry Holding B.V., Ens (NL)

(72) Inventor: Marcel Suiker, Ens (NL)

(73) Assignee: Flevo Berry Holding B.V., Ens (NL)

( * ) Notice: Subject to any disclaimer, the term of this patent is extended or adjusted under 35 U.S.C. 154(b) by 0 days.

(21) Appl. No.: 16/602,204

(22) Filed: Aug. 27, 2019

(51) Int. Cl.
*A01H 5/08* (2018.01)
*A01H 6/74* (2018.01)

(52) U.S. Cl.
USPC ..... Plt./208
CPC ..... *A01H 6/74* (2018.05)

(58) Field of Classification Search
USPC ..... Plt./208, 209
CPC ..... A01H 5/0893
See application file for complete search history.

*Primary Examiner* — Kent L Bell
(74) *Attorney, Agent, or Firm* — Samuel R. McCoy, Jr.

(57) ABSTRACT

A new and distinct *Fragaria* x *ananassa* plant named 'Falco' which is characterized by the combination of mid-season short-day fruiting, a high yield of fruit, very large bright red and glossy fruit, firm fruit, and the stability of these characteristics from generation to generation.

3 Drawing Sheets

Latin name of the genus and species: The Latin name of the genus and species of the novel variety disclosed herein is *Fragaria* x *ananassa.*

Variety denomination: The inventive cultivar of *Fragaria* disclosed herein has been given the variety denomination 'Falco'.

BACKGROUND OF THE INVENTION

Parentage: 'Falco' is the result of a controlled pollination breeding program carried out in April on 2011 in Ens, Netherlands. The new variety originated as a seedling from the crossing of *Fragaria* x *ananassa* '00-102-99' (unpatented), the seed parent, with *Fragaria* x *ananassa* '07-110-07' (unpatented) as the pollen parent. Seed from said cross was harvested, then germinated, and the resulting seedlings were grown to a mature size in order to evaluate for desirable commercial characteristics. In May of 2012, the inventor selected the new *Fragaria* for commercialization. This new and distinctive cultivar was given the name 'Falco'.

Asexual Reproduction: Asexual reproduction of 'Falco', by way of rooting stolon cuttings, was first performed in July of 2012 in Ens, Netherlands. Through seven subsequent generations, the unique features of this cultivar have proven to be stable and true to type.

SUMMARY OF THE INVENTION

The cultivar 'Falco' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Falco'. These characteristics in combination distinguish 'Falco' as a new and distinct *Fragaria* cultivar:

1. *Fragaria* 'Falco' exhibits mid-season, short-day fruiting; and

2. *Fragaria* 'Falco' exhibits a high yield of fruit; and
3. *Fragaria* 'Falco' exhibits very large, firm fruit with a sweet flavor; and
4. *Fragaria* 'Falco' exhibits fruit with a bright red general coloration.

BOTANICAL DESCRIPTION OF THE PLANT

Figure 1:
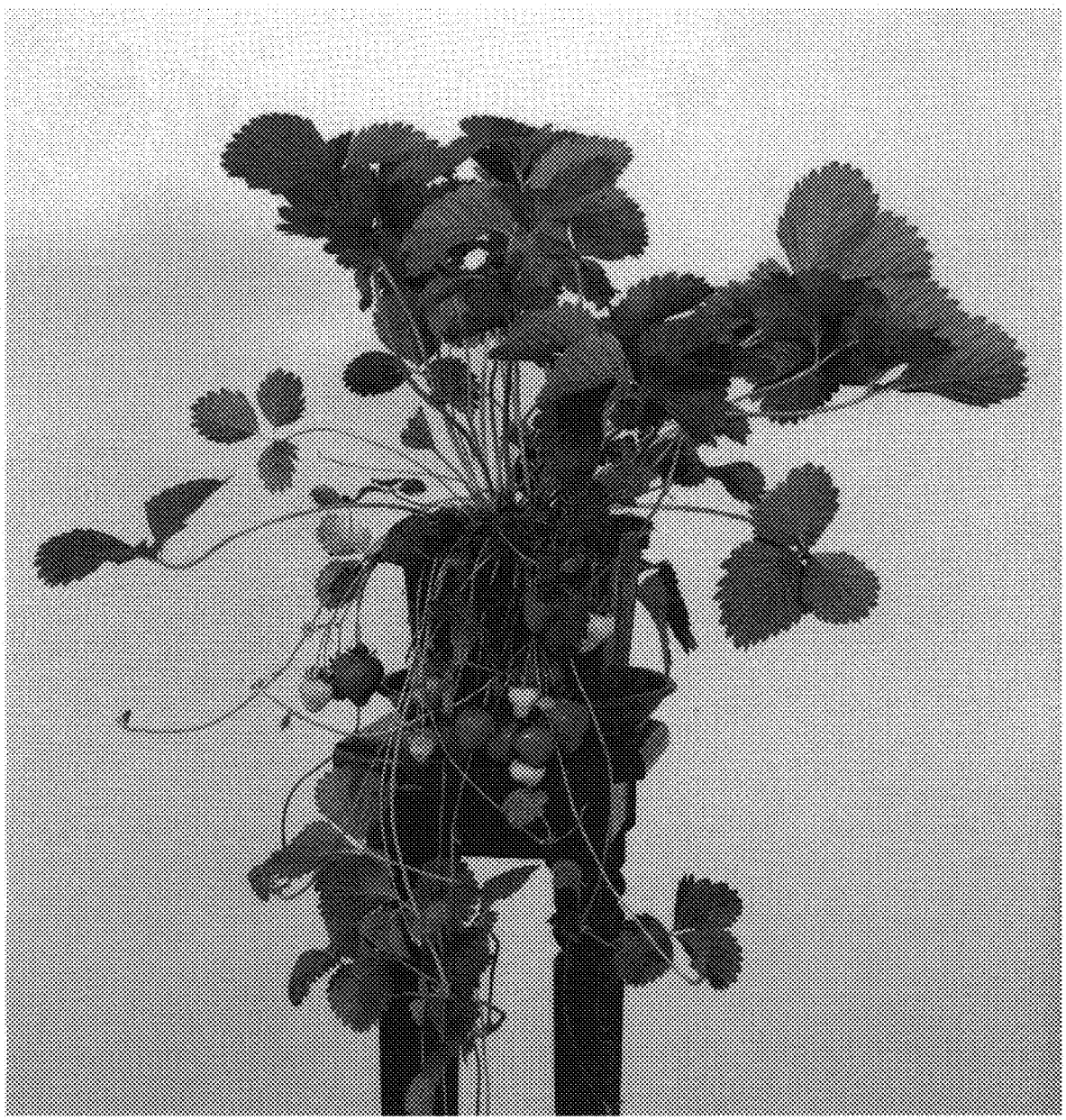
FIG. 1 illustrates, as nearly true as it is reasonably possible to make the same in color photographs of this type, an exemplary 3 month old 'Falco' plant, grown at a commercial greenhouse in Ens, Netherlands.
Figure 2:
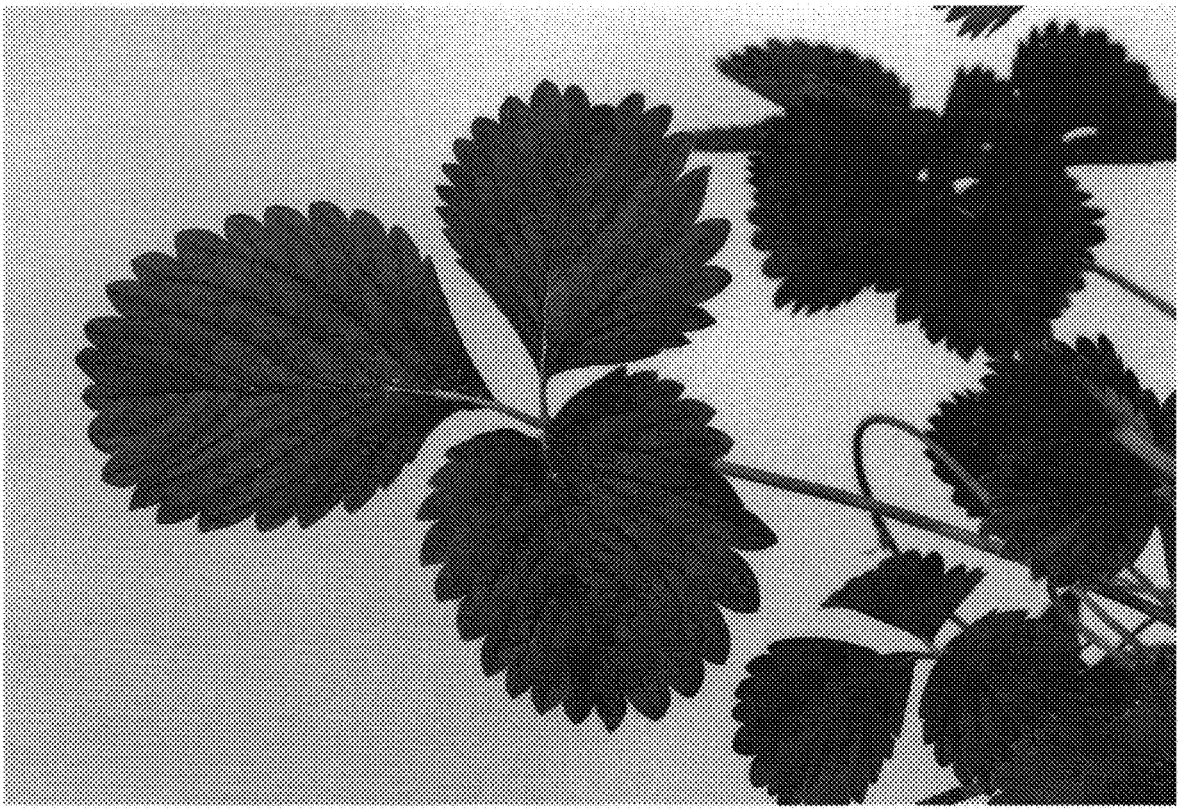
FIG. 2 illustrates, as nearly true as it is reasonably possible to make the same in color photographs of this type, the typical foliage of 'Falco'.
Figure 3:
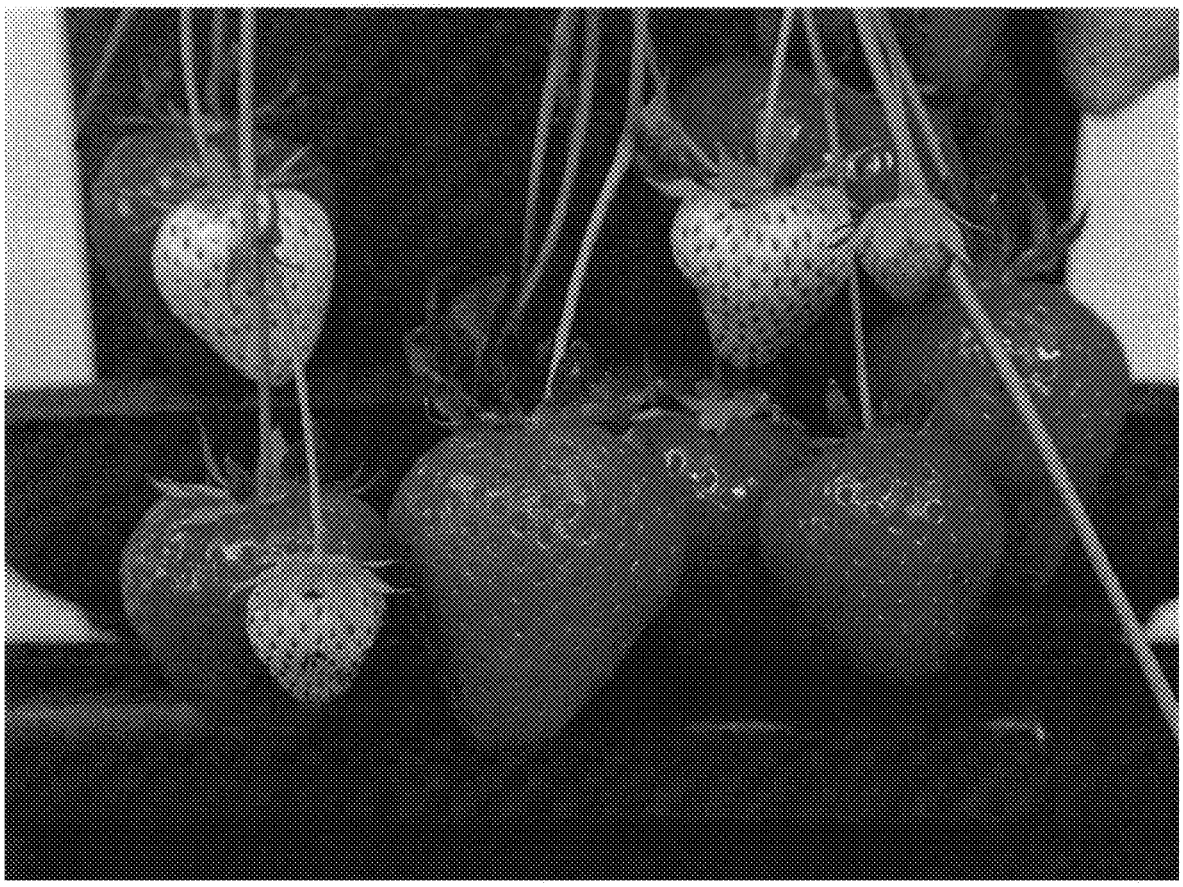
FIG. 3 illustrates, as nearly true as it is reasonably possible to make the same in color photographs of this type, the typical fruit of 'Falco'.

The following is a detailed botanical description of a new and distinct variety of *Fragaria* known as 'Falco', based upon observations of 3 month old greenhouse-grown plants in 250 cc nursery containers, produced in Ens, Netherlands. Plants were grown using conventional greenhouse production protocols for *Fragaria* plants which consisted of drip irrigation, as well as fertigation applications. Biological insect control measures were utilized in production. Plants were produced with full sun exposure and no photoperiodic treatments or artificial light was given to the plants. Observation data was recorded in April of 2018.

Those skilled in the art will appreciate that certain characteristics will vary with older or, conversely, with younger plants. 'Falco' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 edition.

A botanical description of 'Falco' and a comparison with the parent plants and the most similar commercial *Fragaria* cultivar known to the inventor, is provided below.

Plant description:

*Growth habit*.—Acaulescent, stoloniferous perennial; flattened globular shape with leaves and inflorescence developing from basal crowns with approximately 5 crowns per pot; no lateral branching is present.

*Plant form*.—Globular.

*Average height*.—40.0 cm.

*Average width*.—74.0 cm.

*Plant vigor*.—Moderately to highly vigorous.

*Rate of growth*.—Moderately fast growing to fast growing.

*Propagation details*.—Asexual propagation is accomplished by rooting stolon cuttings.

*Time to initiate roots*.—Rooting is initiated in approximately 7 days when grown with an ambient average temperature of 17 degrees Celsius.

*Time to produce a marketable rooted cutting*.—Approximately 30 days to produce a rooted cutting.

*Pest resistance and susceptibility*.—Not any more or less tolerant or susceptible to pests or diseases known to effect *Fragaria* x *ananassa*.

*Environmental tolerances*.—Adapt to USDA Zones 4 through 9 and temperatures ranging from at least minus −32 degrees Celsius to 40 degrees Celsius; low to moderate tolerance to rain; moderate to high tolerance to wind.

Root system:

*Type*.—Moderately fibrous root system.

*Branching*.—Moderately branched.

*Density*.—Moderately dense.

*Distribution*.—Roots distributed evenly throughout the soil profile, from shallow to deep.

*Diameter*.—Largest roots measuring 0.5 mm in diameter.

*Texture*.—Smooth; lacking root hairs.

*Color*.—Greyed-brown, nearest to in between RHS N199C and N199D.

Stolons:

*Length*.—82.0 cm.

*Diameter*.—0.275 cm.

*Texture*.—Moderately covered with adpressed to strigose hairs; average length of hairs is 0.2 cm; colored translucent white, nearest to RHS NN155D.

*Color*.—Yellow-green, nearest to a mixture of RHS 144A and 144B.

Foliage:

*Arrangement*.—Alternate.

*Attachment*.—Petiolate.

*Attitude*.—Upward and outward.

*Division*.—Trifoliate.

*Shape*.—Cordate to reniform.

*Length*.—17.0 cm, excluding the petiole.

*Width*.—20.9 cm.

*Quantity*.—8 leaves per crown.

*Leaflets*.—Quantity — 3. Shape — Broad ovate to near orbicular. Length — 10.8 cm. Width — 9.7 cm. Aspect — Slightly to moderately carinate. Apex — Abruptly acute. Base — Attenuate. Margin — Coarsely crenate to serrate. Texture, adaxial surface — Slightly rugose and sparely covered with very thin, soft hairs with an average length of 0.15 cm; hairs are a translucent white, nearest to RHS NN155D. Texture, abaxial surface — Slightly rugose and moderately covered with very thin, soft hairs with an average length of 0.15 cm; hairs are a translucent white, nearest to RHS NN155D. Luster, adaxial surface — Slightly to moderately glossy. Luster, abaxial surface — Matte. Color — Juvenile foliage color, adaxial surface — Yellow-green, nearest to RHS 144B, and margined slightly darker, nearest to RHS 143A. Juvenile foliage color, abaxial surface — Yellow-green, nearest to RHS 144B. Mature leaf color, adaxial surface — Green nearest to RHS NN137A. Mature leaf color, abaxial surface — Nearest to in between yellow-green, RHS 147B, and greyed-green, RHS 191A. Venation — Type — Pinnate. Vein color, adaxial surface — Yellow-green, nearest to a mixture of RHS 144B and 144C. Vein color, abaxial surface — Yellow-green, nearest to RHS 145B.

*Petiole*.—Length — 29.6 cm. Diameter — 0.42 cm. Strength — Strong. Color, adaxial surface — Yellow-green, nearest to in between RHS 144A and 144B. Color, abaxial surface — Yellow-green, nearest to RHS 144B. Texture, adaxial and abaxial surfaces — Moderately covered with thin, soft strigose hairs with an average length of 0.2 cm; hairs are a translucent greyed-white, nearest to RHS 156D. Luster, adaxial and abaxial surfaces — Moderately glossy.

*Stipules*.—General — Two leafy stipules present at the base of each leaf. Shape — Narrow deltoid. Length — Average of 3.6 cm. Width — Average of 0.4 cm. Apex — Narrowly acute. Base — Broad cuneate. Aspect — Folded. Color, adaxial surface — Greyed-purple, nearest to RHS 185D. Color, abaxial surface — Greyed-purple, nearest to a mixture of RHS 184C and 184D, and veined yellow-green, nearest to RHS 144B. Texture, adaxial surface — Glabrous. Texture, abaxial surface — Glabrous.

Inflorescence:

*Type*.—Compound cymose panicle, generally referred to as a truss.

*Natural flowering season*.—From spring into summer in Ens, Belgium.

*Time to flower*.—9 months.

*Quantity of open flowers per inflorescence*.—3.

*Quantity of buds per inflorescence*.—15.

*Length*.—22.5 cm, including the peduncle.

*Diameter*.—15.9 cm.

*Peduncle*.—Length — 9.0 cm. Diameter — 0.4 cm. Aspect — At an average angle of 65 degrees to horizontal. Strength — Moderately strong. Texture — Densely covered with thin, soft strigose hairs with an average length of 0.2 cm; hairs are a translucent white, nearest to RHS NN155D. Luster — Slightly glossy. Color — Yellow-green, nearest to a mixture of RHS 144A and 144B.

Flower buds:

*Shape*.—Broad ovate.

*Length*.—Average of 1.5 cm.

*Diameter*.—Average of 1.2 cm.

*Texture*.—Moderately covered with thin, soft hairs with an average length of 0.02 cm; hairs are a translucent white, nearest to RHS NN155D.

*Luster*.—Matte.

*Color*.—Green, nearest to a mixture of RHS 138D and 143C, and becoming yellow- green at the base, nearest to RHS 145B.

Flower:

*Form*.—Rotate; single.

*Aspect*.—Upright and outward.

*Flower diameter*.—3.5 cm.

*Flower length*.—1.4 cm.

*Fragrance*.—Slight sweet fragrance.

*Lastingness*.—Approximately 7 days.

*Persistent*.—Self-cleaning.

*Pedicels*.—Length — Varying from 2.6 cm to 15.5 cm. Diameter — 0.15 cm. Aspect — Upward; approximately 45 degrees to the peduncle axis. Strength — Moderately strong. Texture — Densely covered with thin, soft strigose hairs with an average length of 0.15 cm; hairs are a translucent white, nearest to RHS NN155D. Luster — Slightly glossy. Color — Yellow-green, nearest to RHS 144C.

*Petals*.—Arrangement — Rotate with a single whorl of free petals. Quantity of Petals — 6. Shape — Near orbicular to reniform. Length — 1.05 cm. Width — 1.2 cm. Apex — Obtuse. Base — Cuneate. Margin — Entire; lightly undulated. Aspect — Concave. Texture and luster of upper surface — Moderately velvety; matte. Texture and luster of lower surface — Moderately velvety; matte. Petal color when opening, upper surface — White, nearest to RHS NN155C, and slightly darker towards the base, nearest to RHS NN155B. Petal color when opening, lower surface — White, nearest to RHS NN155C. Petal color when fully opened, upper surface — White, nearest to RHS NN155C, and slightly darker towards the base, nearest to RHS NN155B. Petal color when fully opened, lower surface — White, nearest to RHS NN155C. Petal venation color, fully opened, upper surface — Veins are not visible. Petal venation color, fully opened, lower surface — Veins are not visible.

*Calyx*.—Shape — Rotate. Length — 0.7 cm. Diameter — 3.5 cm. Sepals — Arrangement — Rotate with sepals in a single whorl and fused at the base. Quantity — 12. Length — 1.5 cm. Width — 0.6 cm. Shape — Ovate to narrow elliptic. Apex — Acute. Base — Fused. Sepal lobe margin — Entire; not undulated. Texture, upper surface — Sparsely covered with thin, soft strigose hairs with an average length of 0.1 cm; hairs are a translucent white, nearest to RHS NN155D. Texture, lower surface — Sparsely covered with thin, soft strigose hairs with an average length of 0.1 cm; hairs are a translucent white, nearest to RHS NN155D. Luster, adaxial surface — Very slightly glossy. Luster, abaxial surface — Matte. Color when opening, upper surface — Green, RHS 141A. Color when opening, lower surface — Green, nearest to in between RHS 138B and 143C, and becoming yellow-green at the base, nearest to RHS 145B. Color when fully opened, upper surface — Green, RHS 141A. Color when fully opened, lower surface — Green, nearest to RHS 138B, and becoming yellow-green at the base, nearest to in between RHS 145B and 150B.

*Bracts*.—Position — A single bract is present at the base of each pedicel. Shape — Narrow elliptic to narrow ovate. Length — 1.7 cm. Width — 0.5 cm. Apex — Aristate. Base — Broad cuneate. Aspect — Folded. Color, adaxial and abaxial surfaces — Green, nearest to RHS 143B. Texture, adaxial surface — Glabrous. Texture, abaxial surface — Moderately covered with soft adpressed hairs with an average length of 0.1 cm; hairs are a translucent white, nearest to RHS NN155D.

Reproductive organs:

*Stamens*.—Quantity — Approximately 30. Anthers — Attachment — Basifixed. Shape — Ovate. Length — 0.15 cm. Width — 0.1 cm. Color — Orange, nearest to RHS 11A. Filaments — Length — Approximately 0.3 cm. Color — Yellow-green, nearest to RHS 145D. Pollen, amount — None detected.

*Pistil*.—Quantity — 250. Length — 0.1 cm. Style — Length — 0.9 cm. Color — Green-yellow, nearest to RHS 1B. Stigma — Shape — Club-shaped. Length — 0.05 cm. Diameter — 0.05 cm. Color — Green-yellow, nearest to RHS 1A. Ovary Color — Yellow-green, nearest to RHS 144C.

Seed and fruit:

*Fruit*—Harvest Season — Spring in the Netherlands. Fruit Yield — An average of 750 grams of total fruit are produced by each plant in a season. Quantity — An average of 20 per plant. Dimensions — 4.7 cm long and 4.3 cm in diameter. Weight — 22.0 grams. Shape — Globose conic to conical. Texture — Moderately to densely covered with thin, soft hairs with an average length of 0.1 cm; hairs are a translucent white, nearest to RHS NN155D. Luster — Glossy. Color — Immature fruit — White, RHS 157C. Immature flesh — White, RHS 155C. Mature fruit — Red, nearest to a mixture of RHS 45A and N45A. Mature flesh — Orange-red, RHS N34C. Fruit flavor — Moderately sweet and slightly acidic.

*Achenes*.—Position — Below the fruit surface. Quantity of achenes per fruit — Approximately 200. Shape — Flattened; outline is ovate. Length — 0.15 cm. Diameter — 0.08 cm. Texture — Smooth; glabrous. Color — Greyed-orange, nearest to RHS 164B.

COMPARISON WITH THE PARENTS

Plants of the new cultivar 'Falco' may be distinguished from its seed parent, *Fragaria* x *ananassa* '00-102-99' (unpatented), by the characteristics described in Table 1.

TABLE 1

| Characteristic | 'Falco' | '00-102-99' |
|---|---|---|
| Firmness of fruit. | Firmer than '00-102-99'. | Softer than 'Falco'. |
| Fruit size. | Larger than '00-102-99'. | Smaller than 'Falco'. |

Plants of the new cultivar 'Falco' may be distinguished from its pollen parent, *Fragaria* x *ananassa* '07-110-07' (not patented), by the characteristics described in Table 2.

TABLE 2

| Characteristic | 'Falco' | '07-110-07' |
|---|---|---|
| Fruit yield. | Higher yield than '07-110-07'. | Lower yield than 'Falco'. |
| Fruit set of primary flower. | Fruit set is good. | Fruit set is poor. |

COMPARISON WITH THE CLOSEST KNOWN COMMERCIAL COMPARATOR

Plants of the new cultivar 'Falco' may be distinguished from the most similar known commercial comparator, *Fragaria* x *ananassa* 'Elsantra' (not patented), by the characteristics described in Table 3.

TABLE 3

| Characteristic | 'Falco' | 'Elsantra' |
|---|---|---|
| Fruit size. | Larger than 'Elsantra'. | Smaller than 'Falco'. |
| Smoothness of fruit surface. | Smooth. | Rough. |

That which is claimed is:

1. A new and distinct cultivar of *Fragaria* x *ananassa* plant named 'Falco', substantially as described and illustrated herein.

* * * * *